(12) United States Patent
Uji

(10) Patent No.: US 6,431,865 B1
(45) Date of Patent: Aug. 13, 2002

(54) ARTIFICIAL TOOTH

(76) Inventor: Hideyo Uji, 1-16-6F, Ginza 5-chome, Chuo-ku, Tokyo 104-0061 (JP)

(*) Notice: Subject to any disclaimer, the term of this patent is extended or adjusted under 35 U.S.C. 154(b) by 0 days.

(21) Appl. No.: 09/423,627

(22) PCT Filed: Jul. 6, 1998

(86) PCT No.: PCT/JP98/03021
§ 371 (c)(1),
(2), (4) Date: Nov. 16, 1999

(87) PCT Pub. No.: WO98/49882
PCT Pub. Date: Nov. 12, 1998

(30) Foreign Application Priority Data

| Jul. 10, 1997 | (JP) | 9-218875 |
| May 26, 1998 | (JP) | 10-181313 |
| Jul. 6, 1998 | (JP) | 10-225099 |

(51) Int. Cl.[7] ............................................. A61C 13/097
(52) U.S. Cl. ...................................................... 433/169
(58) Field of Search ............................. 433/168.1, 169, 433/170

(56) References Cited

U.S. PATENT DOCUMENTS

| 2,380,468 A | * | 7/1945 | Saffir |
| 3,197,866 A | * | 8/1965 | Barron |
| 3,958,334 A | * | 5/1976 | Heimansohn |
| 4,014,095 A | * | 3/1977 | Heimansohn |
| 4,318,696 A | * | 3/1982 | Kasama et al. ............. 433/173 |
| 5,040,982 A | * | 8/1991 | Stefan-Dogar ............. 433/169 |
| 5,678,994 A | * | 10/1997 | Morehead ................... 433/169 |
| 6,019,604 A | * | 2/2000 | Gougeon ................. 433/168.1 |

FOREIGN PATENT DOCUMENTS

| JP | 54-129798 A | 10/1979 |
| JP | 59-189839 A | 10/1984 |
| JP | 61-265139 A | 11/1986 |
| JP | 4-364838 A | 12/1992 |
| JP | 7-67890 A | 3/1995 |

* cited by examiner

Primary Examiner—Ralph A. Lewis
(74) Attorney, Agent, or Firm—Oblon, Spivak, McClelland, Maier & Neustadt, P.C.

(57) ABSTRACT

A stable dental prosthesis or artificial tooth which makes occlusal adjustment easier and which includes a stress breaking layer made of a flexible buffering material and provided between an occlusal surface portion and a connecting portion of the artificial tooth. The stress breaking layer made of the flexible buffering material can adjust the biting force in response to any varying occlusal pressure, allowing flexibly adjustment of position movement of the occlusal surface portion, and also allowing its vertical, horizontal and oblique movements, while the person wearing the artificial tooth is resting. The artificial tooth also allows easy adjustment of the cusp angle of the occlusal surface portion.

30 Claims, 13 Drawing Sheets

ARTIFICIAL TOOTH

BACKGROUND OF THE INVENTION

1. Field of the Invention

This invention relates to artificial teeth, particularly, artificial teeth being capable of providing occlusal equilibration and pressure buffering function.

2. Discussion of the Background

Artificial teeth such as a full denture or a partial denture so far have generally comprised hard raw materials, say, resin teeth, hard resin teeth, porcelain teeth, metal teeth, or Levin bladed teeth for the purpose of masticating food, the teeth which are embedded in alveolar the denture base for the purpose of masticating food transmit naturally the resulted biting or masticating pressure directly to the dental plate.

Therefore, if one point of the artificial teeth embedded in the alveolar portion of the dental base is only slightly higher than the other parts, the other parts of the artificial teeth embedded in the alveolar portion of the dental base as well as the client's natural teeth can not meet properly nor occlude well because the other major parts are recessed, thereby resulting in the occlusal disproportion because of said higher one point; thus the mucous membrane under the dental base is likely hurt.

An occlusal proportion caused by only one point makes not only the occlusal disproportion but also imbalance throughout the oral cavity.

As some time has elapsed after the artificial denture was fitted up in the mouth, the occlusal disproportion is resulted from the recession or attrition of the occlusal surface, and addition of resin to the resin teeth, replacement of the artificial tooth or teeth, or at last replacement with a new artificial denture must be employed for the treatment. This means that an economic loss, by taking some adjustment time for the client to adapt to the new artificial denture, and thus inviting undesirable burdens of not only the client but also the dentist.

Furthermore, the artificial denture already fitted up must be still used or ground by means of dental machinery when it is needed to provide an appropriate cusp angle suitable to the individual client.

Until now clients can not help having their dentist provide the occlusal equilibration, and it is so difficult for a client to tell the doctor his or her delicate mismatched feeling of occlusion that it takes a lot of time for both of them to get finally a good, stable occlusion.

An example of this kind of artificial denture is as described in Japanese Laid Open Patent Publication No. 7-67890/1995 and the like.

The artificial teeth specified in said Japanese Laid Open Patent Publication NO. 7-67890/1995, as shown in FIG. 1 of the Specification of said Publication, the artificial anterior teeth 11, 12, and 13 in the maxillary site having each a triangular plate at the lingual surface and the artificial anterior teeth 1, 2, and 3 in the mandibular site bite off the eaten food at said triangular flat surface. Artificial teeth 4a, 4b, and 4c in place of the lower first premolar, second premolar and the first molar, respectively, are forming a linked molar band en bloc, and all the molar surfaces are flat. The corresponding artificial tooth 14 in the maxillary site is made as en bloc, a special setting is provided on the molar surface of said artificial tooth 14, thereby the food is ground.

The artificial tooth 5 in place of the mandibular second molar does not touch with the surface of the corresponding artificial tooth 15 when the mouth is closed as in the natural state. When a propensity force towards in one direction is imposed on one front side of the full denture A, said artificial tooth 15 and the corresponding artificial tooth 5 make occlusion, whereby the stability of the full denture A is realized. Such the artificial teeth have been already developed.

The weakness of the full denture and partial denture heretofore specified is as follows; when only one point is slightly higher than the other points, the conditions at the whole parts are inappropriate because the whole parts of the artificial denture are formed with hard, solid materials, and the artificial teeth are embedded solidly in the alveolar portion of the denture base.

As for a full denture formed en bloc, if one point of said full denture is only slightly higher, it affects the whole denture, resulting in instability of the whole artificial denture, thus likely leading to the upset of the whole denture or giving pains to the mucous membrane.

Hence, if only one higher part exists, no treatment for the very narrow point can be done, it gives problems not only to the full denture but also to the whole oral cavity, and prevents the artificial teeth from providing good occlusion.

If no good occlusion is obtained because the occlusal surface is too much recessed at the time of fitting up of a newly prepared artificial denture, or worn out when some time elapsed after the fitting up of the newly prepared artificial denture, a certain amount of resin is added to the artificial teeth for the compensation, or even it must be replaced with a new artificial denture. It is very difficult to keep the best state of occlusion because it is impossible to adjust the occlusal surface portion with a fine tuning for delicate occlusal adjustment corresponding to very slight changes of occlusion and to keep good occlusal equilibration.

When adjusting the cusp angle is individually necessary because of the differences among individual persons, the states of the counterpart teeth, missing teeth, and/or jaws, grinding by means of the dental machinery or addition of the resin or even replacement with newly prepared teeth becomes necessary.

Furthermore, occlusal adjustment of the artificial denture already fitted up can not be performed by the clients themselves, nor can the clients help having their dentist do so.

The artificial teeth specified in the Japanese Laid Open Patent Publication No. 7-67890/1995 should be applied for the full denture, but not for the partial denture at the time said full denture is prepared, and the maxillary and mandibular teeth must be made at the same time. The teeth at one side of the jaw, however, will not function properly, and let alone, only one tooth can not work properly in such the treatment. The artificial teeth have not characteristic properties of the natural teeth, so that they invite problems for most women who love esthetic looking at all times. And occlusal adjustment can not be done by the clients themselves, nor can they help having their doctor do so.

SUMMARY OF THE INVENTION

The first object of this invention is to prevent the artificial teeth of the partial denture and full denture from their premature contacts.

The second object of this invention is to prevent any premature contacts of the artificial teeth, and to provide artificial teeth capable of relieving biting and masticating pressure.

The third object of this invention is to prevent the premature contacts, and to provide artificial teeth capable of relieving biting and masticating pressure, and in addition being capable of adjusting freely the position of the occlusal surface, thus resulting in stability of the occlusion.

The fourth object of this invention is to provide artificial teeth whose occlusal cusp angle being easily adjusted for the very client who requires said artificial teeth or denture.

The fifth object of this invention is to provide artificial teeth being easily adjusted as they should be, and also to provide good occlusion without grinding off the occlusal surface of the artificial teeth or adding any resin to said teeth.

The sixth object of this invention is to provide proper occlusion of the artificial teeth being adjusted easily not only by the doctor but also by any client himself or herself.

To achieve the above and other objects, the present invention includes a structure so designed that pressure-buffering layer, which is provided between the occlusal surface portion that received biting pressure and/or masticating pressure and the bonded part that connected to the alveolar portion of the denture base, is made of flexible material capable of buffering any pressure resulted from occlusal force or biting-pressure, and transmitting the reduced pressure to the denture base for the purpose of achieving the first object of this invention stated beforehand.

If one of the teeth happens to make a premature contact and an excessive occlusal force is imposed onto the occlusal surface, the stress breaking layer made of flexible pressure-buffering material becomes elastic and deformed, and this makes it possible for the occlusal surface to recess, moving downwards, thus making the occlusal surface be stopped at the desirable equilibration so that the remaining teeth are totally in the uniform occlusion.

In order to achieve the second object stated beforehand, a shock absorbing system made of flexible buffering material, which is a kind of spring-action element, is provided in said pressure-buffering layer, thus a functional mechanism, which is capable of adjusting the intensity of the stress breaking action, is provided in said shock absorbing system.

In order to achieve the third object stated beforehand, a shock absorbing system made of flexible buffering material, which acts as a kind of spring, is provided in said stress breaking layer and a functional mechanism, which is capable of adjusting the intensity of the stress breaking action, is provided in said shock absorbing system. In addition, an adjusting mechanism provided in the shock absorbing system that is capable of moving freely, including vertical, horizontal, and/or oblique movement, thus capable of making the occlusal surface be moved freely and controlled properly.

In order to achieve the fourth object of this invention stated beforehand, the cusp angle of the occlusal surface is made adjustable.

In order to achieve the fifth object of this invention stated beforehand, the cusp angle of the occlusal surface is made adjustable, and a mechanism that is vertically movable upwards and downwards is provided between said occlusal surface and the connected part. As for said vertically movable mechanism, there are two mechanisms, one mechanism is capable of moving the occlusal surface up-and-down by means of a screw jack, and the other mechanism is capable of moving freely the position of the occlusal surface vertically, horizontally, and/or obliquely.

Furthermore, in order to achieve said fifth object, artificial teeth having a stress breaking layer and said adjusting mechanism can be manufactured in this invention.

In order to achieve the sixth object in this invention stated beforehand, any client is also allowed to be able to adjust the artificial teeth in this invention by himself or herself for the purpose of achieving the second, third, fourth, and fifth objects in this invention as stated beforehand.

The stress breaking layer comprising pressure-buffering material made of elastic raw material, capable of elongating and shrinking freely to some extent, has the function of both properties such as the mass element and spring element. Therefore, the pressure buffering material made of the elastic raw material, capable of elongating and shrinking freely in this invention, has an elastic property as a mass element and a spring property that acts as the spring element.

The elastic material in this invention means non-metallic springs made of composite materials, rubber and rubber analogs, and/or synthetic high-polymers capable of accumulating energy by changing the volume of their bodies. Urethane, silicon, and elastomer plastics are naturally included in this kind of material.

The spring in this invention means a mechanical element capable of accumulating energy by changing their geometry such as the length.

Belleville springs, coil springs, shock absorbers, pneumatic springs, flat springs, torsion bars, bar springs, volute springs, and shape memory alloys, are included in this category of said springs in this invention.

As for the springs, there are three cases; one of them in which individual springs are used independently according to the intensity of the occlusal pressure, the second case in which a spring system capable of adjusting the stress of the springs from the outside force according to the intensity of the occlusal pressure by means of setting-up springs inside the main springs, and the third case in which the springs provided in the main spring, capable of adjusting their strength of spring action, and also moving their position i.e. capable of moving freely, including vertical, horizontal, and/or oblique movement, according to the intensity of the occlusal pressure as adjusted by an outside force.

Hence, for the stress breaking layer made of flexible material, capable of elongating and shrinking freely to some extent, any forms or any materials are suitable as long as said forms and/or materials suitable to the functions stated beforehand, and the system can be made of only elastic materials, and any combinations of any elastic materials and springs can be employed in this invention.

As for said springs in this invention, their reactionary stress to meet the intensity of the occlusal pressure, is adjustable from the outside of the dental corona.

In addition, in this invention a flexible pressure buffering material is provided at the proximal surface so that it allows the occlusal surface to recess freely to some extent, although the undesirable frictional force caused by said proximal teeth does sometimes prevent to do so, when the occlusal surface of the artificial teeth should recess vertically by the occlusal pressure and/or masticating pressure.

As for the proximal surface, some composite materials, rubber and/or rubber analogs, or synthetic resins as the mass element are provided for this purpose, or the occlusal surface that should recess are formed to avoid the surface portion of the proximal teeth.

Artificial teeth for artificial denture with an adjusting mechanism that are capable of allowing the occlusal surface to move freely, including vertical, horizontal, and oblique movements between the occlusal surface and connecting portion, can also be manufactured.

Furthermore, artificial teeth can be so fabricated that they have a combination of the stress breaking layer and the adjusting mechanism.

Artificial teeth whose adjusting mechanism capable of moving freely, including vertical, horizontal, and/or oblique movement, and artificial teeth whose adjusting mechanism is capable of only vertical movement, or only horizontal movement, or only oblique movement are also available, and the artificial teeth whose mechanism is capable of only two kinds of movements out of the vertical, horizontal, and oblique movements are available, too.

As for the mechanism for adjusting the vertical movement of the occlusal surface, any of the following can be applied; screw jack, link-work up-and-down mechanism, cam-work, gear-work and the like that are capable of fine-adjusting, keeping the once-adjusted status intact, and not changing said status by any factors other than the renewal procedure of the adjusting.

The cusp angle is allowed to be changed freely so that the cusp angle of the occlusal surface is adjustable in order to stabilize the occlusion. It is desirable to employ a method to change the angle of the cusp portion by means of the screw jack by letting the central groove of the occlusal surface be the pivotal point.

As for the adjustment of the cusp angle, there are such cases; the case in which the individual cusp is adjustable with regard to the molar teeth, the case in which the cusp angles at either side of the bucca, and the cusp angle including the two cusp angles at either side of the lingua are adjustable independently, and the case in which when the cusp angle of the premolar and/or molar teeth at both sides of the bucca is adjusted, the cusp angle of the cusp at the lingua is adjusted by the same angle as said adjustment at the buccal sides in relation with each other.

Denture manufacturing need not be so much modified for practicing the artificial teeth and dentures as stated in this invention, but will enable the dentists and clients themselves to set up the artificial teeth or dentures in their mouth and to adjust the occlusion by themselves, thus the problems involved in the preparing and wearing the conventional artificial teeth and dentures will be solved by this invention.

DESCRIPTION OF THE PREFERRED EMBODIMENTS

Figure 1:
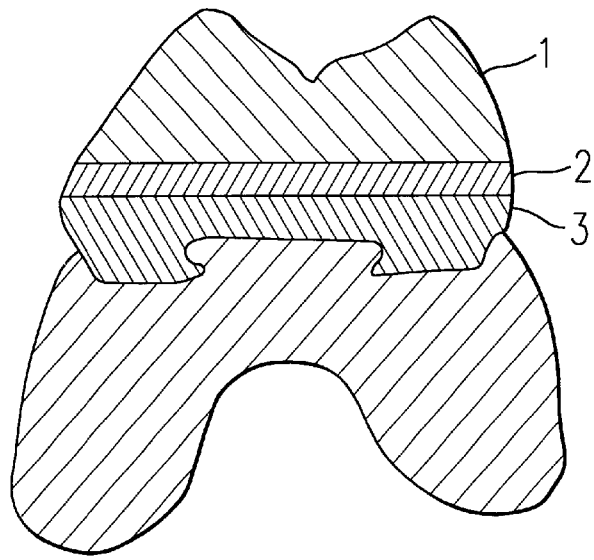
FIG. 1 shows a vertical sectional view of a molar tooth in an embodiment of the artificial teeth of this invention.

The embodiments of this invention are described as follows, referred to the drawing illustrated beforehand.

FIG. 1 shows vertical cross section of the desirable artificial tooth substituting a molar tooth in this invention, in which basically constituted are the stress breaking layer 2, which is made of flexible material capable of elongating and shrinking smoothly, between the occlusal surface 1 receiving directly the masticating pressure and/or occlusal pressure and the connecting portion 3 solidly attached to the alveolar section of the denture base. This figure shows that the basic artificial tooth embodying the form of this invention is emphasized with a simple schematic diagram as simple as possible of the occlusal surface section 1 and the stress breaking layer 2, which is made of flexible buffering material capable of elongating and shrinking smoothly, for the purpose of better comprehension of this invention.

When the occlusal surface section 1 of the artificial molar tooth already fixed up in the oral cavity is pressed with an excessive occlusal pressure as a result of an early contacts, the stress breaking layer 2 will have an elastic deformation, making the occlusal surface portion 1 recess vertically so that the rest of the natural teeth and/or artificial teeth can make a uniform occlusion, and the further movement of the occlusal surface section 1 stops at such the occlusal equilibration.

Furthermore, the intensity of the recession of the artificial teeth in this invention is capable of being self-adjustable. In addition to it, the mechanism capable of moving vertically, horizontally, and obliquely for proper adjustment in the case of occurrence of a largely aberrant occlusal surface portion 1, and another additional mechanism to adjust the cusp angle as well for the purpose of getting an occlusion of better stability, can be set up in this invention.

There are two cases of employing materials; one case in which the materials for the occlusal surface portion 1 are simply those materials such as resins, hard resins, porcelain, and metals as in the form of a simple material, and some combined materials such as a combination of resins and dental metals.

The cusp angle of the occlusal surface portion 1 is adjustable as follows; the occlusal surface portion is prepared according to each cusp angle of the teeth, and the cusp angle that is adjustable by means of the incorporated screw and the like that are adjustable freely by an operation from the outside.

One of the formations of the occlusal surface portion 1 has plurally divided portions according to such as lingual side and buccal side as being divided by the central sulcus and said divided portions being combined en bloc and the said portions are made independently of pressure buffering materials capable of elongating and shrinking smoothly, and the other is not divided, but forms simply one block of the occlusal surface portion.

The buffering material capable of elongating and shrinking smoothly for the stress breaking layer 2 has the function of mass element and spring element.

One of the said pressure buffering materials consists of elastic materials such as composite materials, robber and its analogs, and plastics as mass element and of simply non-metallic spring.

The other can employ the combination of some materials as mass element and springs as spring element.

When the materials are combined with the mass element and the spring element, the stress of the spring given by the occlusal pressure according to the intensity of the occlusal pressure is adjustable by an operation from the outside, and also the length of the spring itself is adjustable by an operation from the outside.

This means that there is a mechanism capable of moving vertically so that the height of the occlusal surface is movable upward and downward in this invention. There is also a mechanism that can be fabricated in the stress breaking layer 2, being capable of adjusting vertical, horizontal, and oblique movements of the occlusal surface portion 1 that is adjustable by an operation from the outside.

There are cases; for example, one case in which the mechanism capable of adjusting freely the movements including the vertical, horizontal, and oblique movements of the occlusal surface portion is fabricated in the stress breaking layer 2, and the other case in which besides the stress breaking layer 2, an additional stress breaking mechanism is fabricated between the occlusal surface portion 2 and the connecting portion, and the said mechanism is capable of adjusting the movements including the vertical, horizontal, and oblique movements.

The artificial teeth can be manufactured as only one artificial tooth and connected teeth of two or more teeth, and only the occlusal surface portion can be also manufactured.

The exchangeable types in which the occlusal surface portions and stress breaking layers are made individually and they are capable of being put on to and put off easily from the oral cavity. In one case of this invention, when the connecting portion 3 is solidly connected to the alveolar section 4 of the denture base, the occlusal surface portion 1 and the stress breaking layer 2 of an artificial tooth are made en block, and the said occlusal surface portion 1 and said stress breaking layer 2 are capable of being put on and off at any time, and in the other case, said occlusal surface portion 1 and stress breaking portion 2 can be made separately, and being able to be independently put on and put off, whereas said stress breaking layer 2 is so made up that it is capable of functioning well as a stress breaking unit en bloc.

When said occlusal surface portion 1 of the fixed up artificial teeth is abraded and worn away and/or when the buffering ability of the stress breaking layer is reduced, it is possible to replace with new one for said occlusal surface portion 1, and also said occlusal surface portion 1 and said stress breaking layer 2 that are made en block are replaceable. It is also possible to replace only said stress breaking layer 2 being made to be removable with new one.

Figure 2:
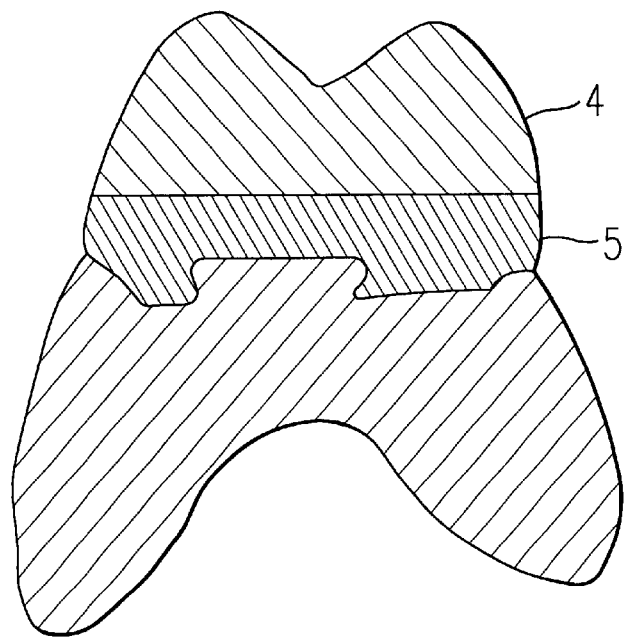
FIG. 2 shows a vertical sectional view of a molar tooth in an embodiment of the artificial teeth of this invention.

In the embodiment as shown in FIG. 2, this embodiment characterizes the property of the artificial molar tooth that the cross-section of the said artificial molar tooth having an occlusal surface portion 4 and a stress breaking layer 5, made of flexible material capable of elongating and shrinking, which is basically connected to the part of the alveolar portion of the denture base.

Said occlusal surface portion 4 is broken down into two kinds; the one in which the occlusal surface portion is made according to each cusp angle, and the other, in which the cusp angle is freely adjustable with an adjusting screw and the like by means of an operation from the outside.

There are two kinds of materials for said occlusal surface portion 4; one kind is made of resins, hard resins, porcelain, or dental metals as in the form of a simple material, and the other is a combination of the resins and the dental metals.

The dental metals hereby mean that they do not include mercury, but include palladium alloys, silver alloys, gold alloys, platinum-added gold alloys, titanium, and the like.

As for the formation of said occlusal surface portion 4, in one case it is divided into plural portions according to such as the lingual side and buccal side, as the central sulcus is taken as the demarcating line, and the said portions are connected each other with some buffering material capable of elongating and shrinking smoothly, and in the other case they are combined en block.

A portion of said stress breaking layer 5 is connected solidly to the inside of the alveolar section of the denture base, thus making the artificial teeth and the artificial denture base be ell bloc.

In such the case, the rest of the stress breaking layer does not enter the inside of the alveolar section so that the alveolar portion is prevented from contacting with any part of the occlusal surface portion when the occlusal surface portion tends to deform and/or recess, because the said occlusal surface portion is pressed by the occlusal pressure and/or masticating pressure.

As for elastic materials as mass element capable of accumulating energy by the way of changing their volume, materials such as composite materials, rubber and its analogs, and springs of non-metallic plastics are employed as their elastic buffering materials capable of elongating and shrinking smoothly for the purpose of said stress breaking layer 5.

Springs as spring element such as belleville springs and shock absorbers, being capable of storing energy by the way of changing physical property such as their length, can be also employed in this invention.

Moreover, the stress breaking layer can be formed by combining the mass element and the spring element.

As for the spring element, it is possible, for example, in the shock absorber, to fabricate a mechanism capable of adjusting the stress of the occlusal pressure according to the intensity of the said occlusal pressure, as being adjustable by an operation from the outside, and it is also possible to fabricate another mechanism that is capable of adjusting, while the client rests, the vertical, horizontal, and oblique movements of the occlusal surface portion with the length of the shock absorber being adjustable by an operation from the outside.

The above described embodiment of this invention brings forth the desirable, proper occlusal equilibration of any clients.

Figure 3:
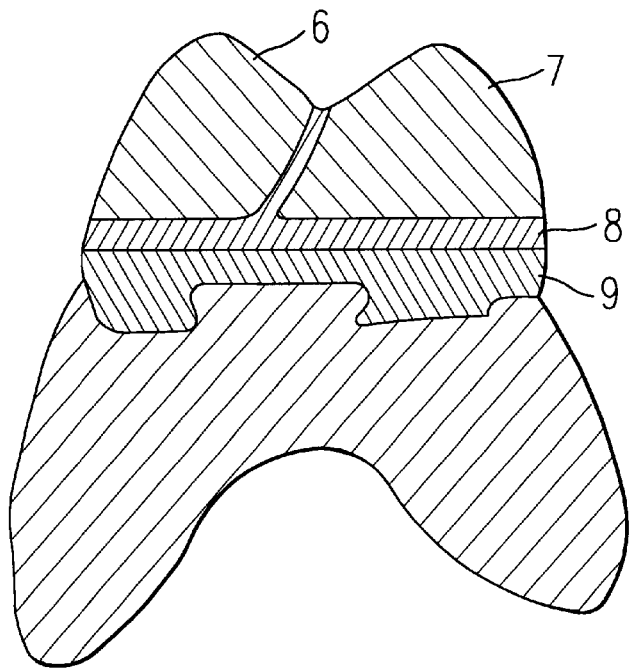
FIG. 3 shows a vertical sectional view of a molar tooth in an embodiment of the artificial teeth of this invention.

Regarding the embodiment of this invention shown in FIG. 3, occlusal surface portion 6 and 7 are divided into plural number, and said divided surface portions are connected with pressure buffering materials capable of elongating and shrinking smoothly so that said connected portions build up the integrated occlusal surface portion.

A stress breaking layer 8 represents a characteristic feature of the artificial tooth of this invention that said stress breaking layer 8 consists of pressure buffering materials capable of elongating and shrinking smoothly and is set up between the occlusal surface portion and the connecting portion.

The artificial tooth can suitable to the variety of the delicate occlusion as a result of the fact that the occlusal portion is divided and consists of several pieces. Said stress breaking layer 8 consisting of pressure buffering materials capable of elongating and shrinking smoothly is made up of as follows; one case in which composite materials, rubber and its analogs, and synthetic plastic materials as the mass element are used, and another case in which belleville springs and shock absorbers as the spring element, and still another case in which combinations of the mass element and spring element are used.

The intensity of the stress in a shock absorber to meet the occlusal pressure is adjustable by an operation from the outside when the shock absorbers are employed, allowing the occlusal surface portion to move vertically with the stress breaking force being kept at a constant, while the client rests, and furthermore in another case fabricated is a mechanism that allows the occlusal surface portion to move horizontally and obliquely.

Figure 4:
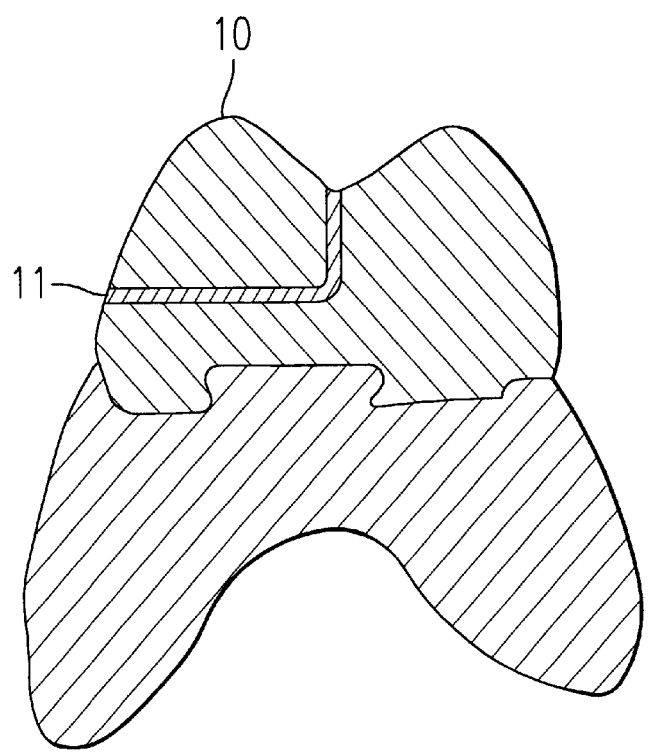
FIG. 4 shows a vertical sectional view of a molar tooth in an embodiment of the artificial teeth of this invention.

In the embodiment of this invention shown in FIG. 4, fabricated is a stress breaking layer, capable of elongating and shrinking smoothly, between a connecting portion and a occlusal surface portion 10 shown in the cross sectional view of the artificial molar tooth illustrated in said figure that is connected to the remaining part of the occlusal surface portion with said pressure buffering materials capable of elongating and shrinking smoothly.

As for the position of said occlusal surface portion 10, there are several cases; it can be located at the functional cusp, at the non-functional cusp, at the cusp of the mesial buccal side, at the cusp of the distal buccal side, at the cusp of the mesial lingual side, or at the cusp of the distal lingual side.

As for a stress breaking layer 11, it can be made up of such as the mass element, the spring element, the mass element and the spring element, and the spring element having an adjusting mechanism capable of moving vertically, horizontally, and/or obliquely.

Figure 5:
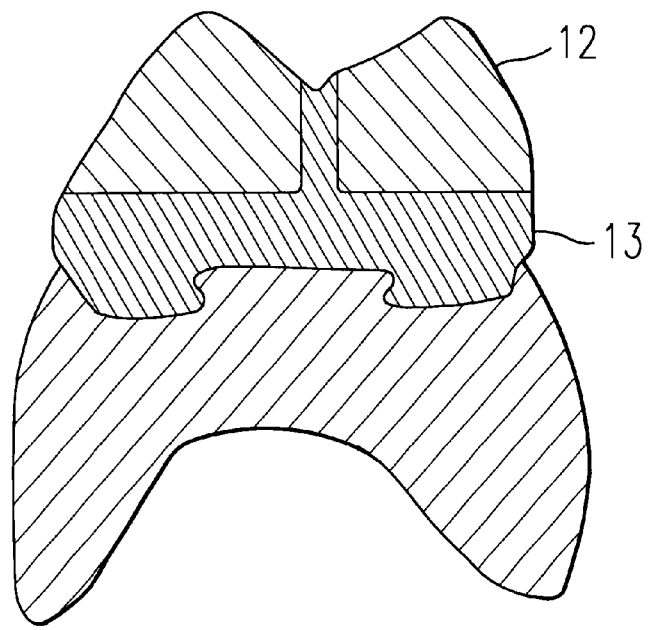
FIG. 5 shows a vertical sectional view of a molar tooth in an embodiment of the artificial teeth of this invention.

The embodiment of this invention illustrated in FIG. 5 is showing artificial tooth consisting of an occlusal surface portion 12 and a stress breaking layer 13, the occlusal surface portion in the cross sectional view of the artificial molar tooth is divided into some pieces, and said divided portions are connected with the pressure buffering materials capable of elongating and shrinking smoothly, thus build up an integrated occlusal surface portion.

A portion of said stress breaking layer 13 forms the connecting portion as it attached tightly to the alveolar portion of the denture base. The remaining stress breaking layer 13 sits on over the alveolar portion, and helps to prevent said occlusal surface 12 from sinking downwards when it receives the occlusal pressure.

Said stress breaking layer 13 is made up of variety of elements and materials such as the mass element, spring element, both mass element and spring element, or the spring element having a mechanism capable of moving vertically, horizontally, and obliquely.

Figure 6:
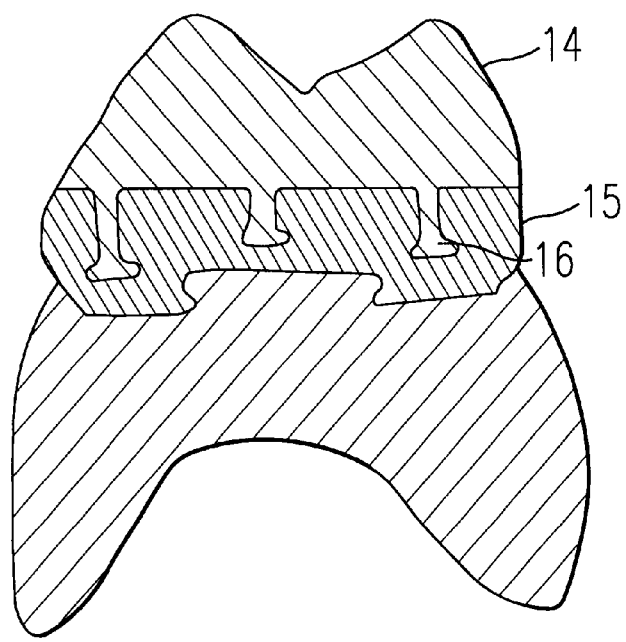
FIG. 6 shows a vertical sectional view of a molar tooth in an embodiment of the artificial teeth of this invention.
Figure 7A:
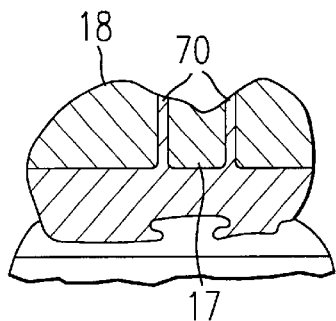
FIG. 7 shows vertical sectional views of two molar teeth and top surface views thereof in an embodiment of the artificial teeth of this invention.
Figure 7B:
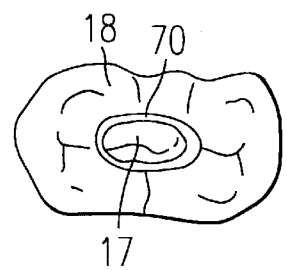
Figure 7C:
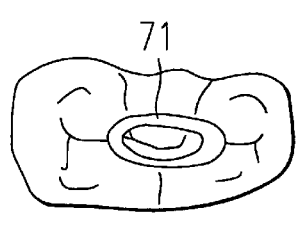
Figure 7D:
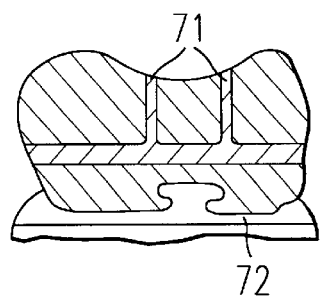

In the embodiment of this invention shown in FIG. 6, the artificial tooth consists of an occlusal portion 14, a stress breaking layer 16, and part of said occlusal surface portion 14 that acts as anchors, which stretch out to a stress breaking layer 15.

Such the structure with said anchors is used for the mechanism capable of adjusting the degree of the recession and the occlusal pressure with the stronger binding force and the variety of width and length of said anchors that can be made as in the variety of geometry.

In the embodiment of this invention shown in FIG. 7-A, the artificial molar tooth consists of the inner part of a dental corona 17, whose central part of the occlusal surface portion being nearly circular, and divided from the rest of the occlusal surface portion, but connected with the rest of the part with pressure buffering materials capable of elongating and shrinking smoothly, and thus it consists of the outer part of a dental corona 18. A stress breaking layer 70 can be so made that it enters the inside of denture base, thus resulting in one integrated block.

As the occlusal pressure imposed upon the occlusal molar tooth, not having elasticity, and forming the proximal surface portion made up of pressure buffering materials capable of elongating and shrinking smoothly, is provided at the upper part of the side of the occlusal surface portion to avoid the contacting point at the proximal surface when said proximal portion of the stress breaking layer is to sink downwards because of the occlusal pressure.

Figure 9:
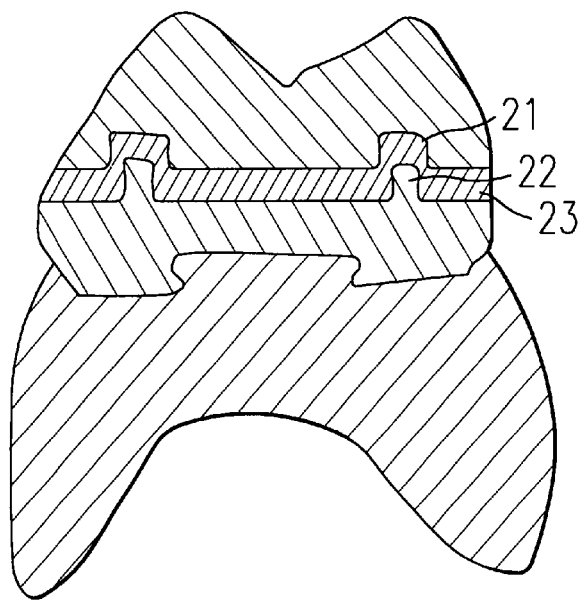
FIG. 9 shows a vertical sectional view of a molar tooth in an embodiment of the artificial teeth of this invention.

In the embodiment of this invention shown in FIG. 9, concave portions 21 and convex portions 22 are provided at an occlusal surface portion 24 of the artificial molar tooth so that the occlusal surface portion sinks downwards being guided by said concave and convex portions when the occlusal surface has to sink downwards. This prevent the occlusal surface portion flora moving laterally in order not to move too far, when the occlusal surface portion has to move laterally.

Figure 10:
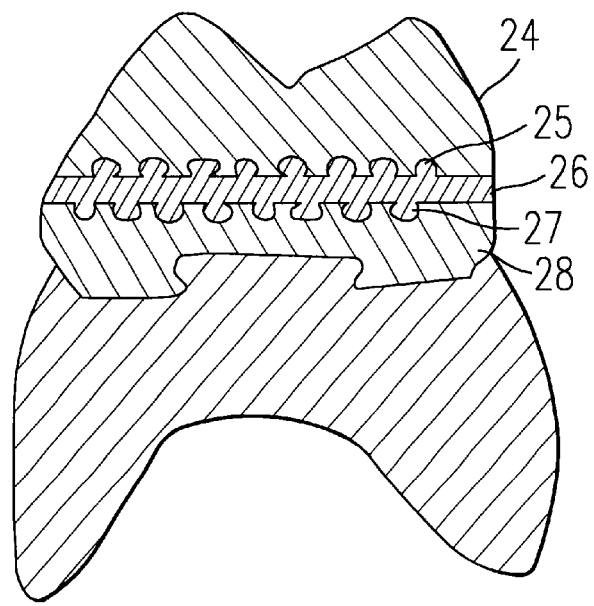
FIG. 10 shows a vertical sectional view of a molar tooth in an embodiment of the artificial teeth of this invention.

In the embodiment of this invention shown in FIG. 10, inner-holding holes inside the occlusal surface portion are provided in said occlusal surface portion 24 of the artificial molar tooth, and inner-holding holes 27 inside a connecting portion are provided in a connecting portion 28, and then the same elastic materials as used in a stress breaking layer 26 is impregnated into said holes, thus resulting in the stronger bonding with each other not only chemically but also physically. surface portion is divided, any delicate occlusal equilibration can be successfully obtained.

FIG. 7-B is a bird's-eye view of FIG. 7-A.

Figure 8:
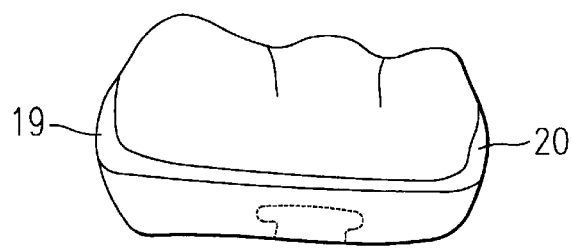
FIG. 8 shows a three-dimensional view of a molar tooth in an embodiment of the artificial teeth of this invention.

FIG. 8-C shows modified figures of FIG. 7-A and FIG. 7-B having a connecting portion 72.

FIG. 8-D is a bird's-eye view of FIG. 8-C.

FIG. 8 is a view of an artificial molar tooth as seen from the buccal side. A mesial proximal surface stress breaking layer 19 is fabricated at the mesial proximal surface, and a distal proximal surface stress breaking layer 20 at the distal proximal surface.

Such the fabrication prevents the occlusal surface portion from rubbing and scrubbing with the artificial teeth neighboring the mesial proximal surface and distal proximal surface, in the case it would not sink downwards smoothly when the occlusal surface portion should sink downwards by the pressure of the occlusion.

Said stress breaking layers at the proximal surface enable an artificial tooth to perform smoothly their capability at the time of the occlusion. Said portions are made up of the mass element such as the composite materials, synthetic plastic materials, rubber and its analogs, and/or pressure buffering materials in a case.

Figure 11:
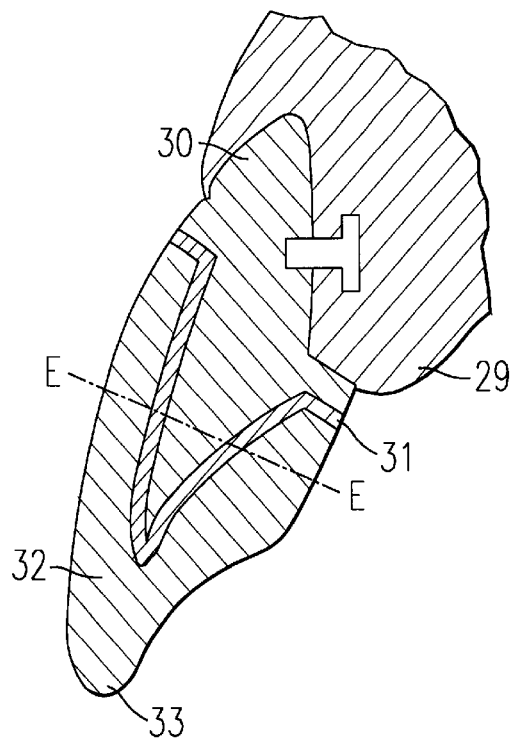
FIG. 11 shows a vertical sectional view of anterior tooth in an embodiment of the artificial teeth of this invention.

And in another case, the proximal portion of the occlusal surface portion can sink downwards at the upper part by the contacting point at the proximal surface, thus being prevented from contacting the proximal tooth or teeth. And part of the artificial As for the embodiment of this invention shown in FIG. 11, this figure shows the cross sectional view of the artificial anterior tooth concerning the basic concept of this invention, in which a stress breaking layer 31 is provided between a connecting portion 30 attached tightly to the alveolar portion of the denture base and a dental corolla 32 that receiving directly the biting pressure and/or masticating pressure, however, said stress breaking layer 31 is illustrated here as simple as possible for the purpose of better comprehension.

Said stress breaking layer 31 made up of the pressure buffering materials capable of elongating and shrinking smoothly can deform itself elastically, and said dental corona 32 moves, but stops at the proper position so that the remaining natural teeth and/or artificial teeth make the desirable occlusal equilibration when said dental corolla 32 of the artificial anterior tooth in the mouth is pressed with an excessive pressure resulted from the early contact.

Moreover the intensity of the sinking downwards force imposed upon the artificial anterior tooth can be made adjustable, and in addition to it, the dental corolla of said artificial anterior tooth is adjustable being capable of moving vertically, horizontally, and/or obliquely with smoothness, while the client rests.

Said dental corona 32 can be made up of such materials as resin, hard resin, porcelain, and metals as the simple material, and any combinations of two or more kinds of materials that are prosthetic compounds, for example, such as resins and dental metals.

Said stress breaking layer 31, consisting of the pressure buffering materials capable of elongating and shrinking smoothly, can be made up of non-metallic spring such as the materials as composite materials, rubber and its analogs, and synthetic plastics, i.e. elastic materials as the mass element capable of accumulating energy by means of changing its body volume. In another case it is made up of the mechanical elements, the spring element such as belleville springs, coil springs, shock absorbers, and shape memory alloys, capable of accumulating energy by means of changing the physical properties such as their length.

Still in another case, it is made up of combinations of the mass element and spring element, and in addition to them, for example, the shock absorbers that are modified as they should be adjustable with regard to the stress to meet the occlusal pressure.

And another mechanism capable of allowing the dental corona to move vertically, horizontally, and obliquely, while client rests, is provided as the mechanical element in this invention.

The following is a characteristic property of this invention concerning the cross sectional view of the artificial anterior tooth. Said stress breaking layer 31 and the adjusting mechanism that enables the dental corona to move vertically, horizontally, and/or obliquely, are provided between said connecting portion 30 and said dental corona 32.

The proximal teeth and the proximal surface neighboring the artificial teeth are made up of the mass element such as composite materials, synthetic plastics, and robber and its analogs that are capable of elongating and shrinking smoothly.

As the proximal surface portions are formed with the part of the connecting portion, and the dental corona which sinks downwards and moves to some extent is formed mainly at both surfaces of the labial and lingual sides in a case, and in another case the pressure buffering materials capable of elongating and shrinking smoothly are formed at the surface behind reaching said proximal surface that includes the contacting point so that the dental corona, while sinking downwards, may not contact the proximal surface(s).

Figure 12:
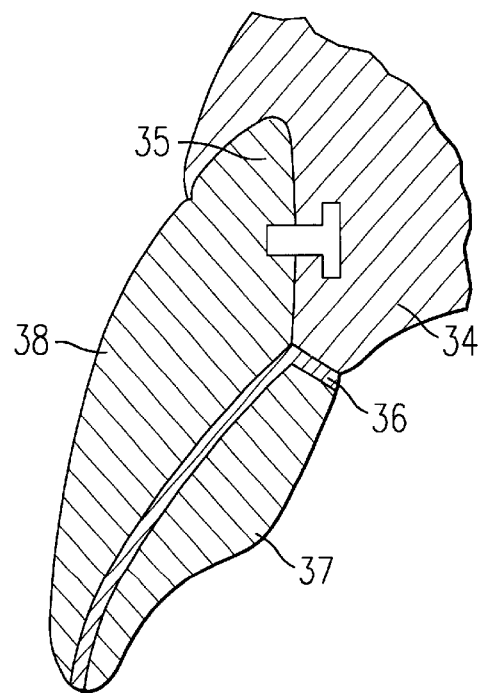
FIG. 12 shows a vertical sectional view of anterior tooth in an embodiment of the artificial teeth of this invention.

The embodiment of this invention in FIG. 12 is showing the cross sectional view of an artificial anterior tooth, is concerning the artificial anterior tooth that has a stress breaking layer 36 capable of elongating and shrinking smoothly, being fabricated between a labial portion 38, extending from a connecting portion 35 attached solidly to the alveolar portion of the artificial denture base, and a lingual portion 37.

When said lingual portion 37 receives an excessive biting pressure and/or masticating pressure, said stress breaking layer 36 made up of the pressure buffering materials capable of elongating and shrinking smoothly deforms itself elastically, and said lingual portion 37 moves and recesses, thus the rest of the natural teeth and/or artificial teeth come into a stable occlusal equilibration.

As for said stress breaking layer 36, there are some cases, namely a case in which elastic materials as the mass element such as composite materials, rubber and its analogs, and synthetic plastics are employed, another case in which both mass element and spring element are employed. Furthermore another case in which a mechanism incorporated in the spring element capable of adjusting the intensity of the stress resulted from the occlusal pressure and it is also capable of adjusting the position of said lingual portion 37 while the client rests.

This position-adjusting mechanism may be incorporated in said stress breaking layer 36, and both stress breaking layer 36 and position adjusting mechanism are to be set up between said labial portion 38 and said lingual portion 37.

Figure 13:
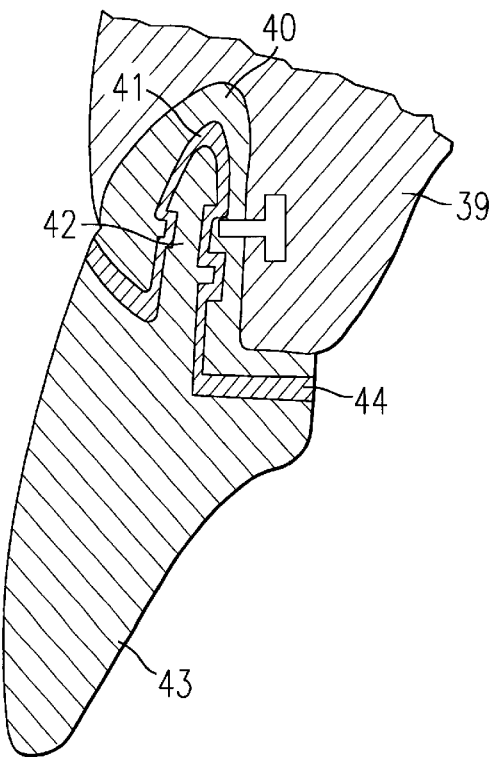
FIG. 13 shows a vertical sectional view of an anterior tooth in an embodiment of the artificial teeth of this invention.

The embodiment of this invention illustrated in FIG. 13 is showing an artificial anterior tooth with a cisal of a dental corona 43 having a cisal edge base 42 that is characterized in that it has a stress breaking layer 41 made up of the pressure buffering materials capable of elongating and shrinking smoothly being provided in a connecting portion 40 that is attached solidly to the artificial denture base.

Figure 14:
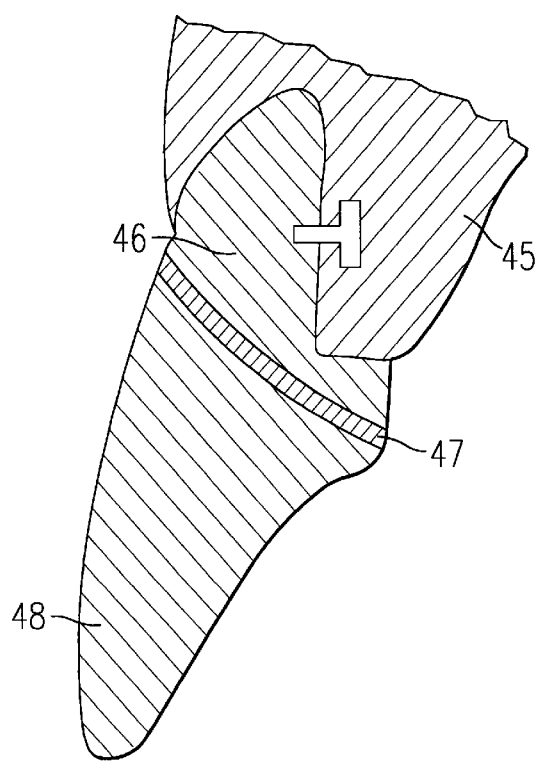
FIG. 14 shows a vertical sectional view of an anterior tooth in an embodiment of the artificial teeth of this invention.

The embodiment of this invention illustrated in FIG. 14 is showing the cross sectional view of an artificial tooth is characterized in that a stress breaking layer 47 made up of the pressure buffering materials capable of elongating and shrinking smoothly is provided between a connecting portion 46 and the dental corona.

As for said stress breaking layer 47, said layer 47 is made up of such materials as composite materials, rubber and its analogs, and synthetic plastics as the mass element in a case, and shock absorbers as the spring element are incorporated in another case.

Combinations of the spring element and the mass element are used in another case. A mechanism in the spring element capable of adjusting the intensity of the stress to meet the occlusal pressure is still incorporated in another case.

This embodiment has another mechanism enabling a denture corolla 48 to move vertically, horizontally, and obliquely freely, and said denture corona being adjustable by an operation from the outside.

As for the position adjusting mechanism of said denture corona 48, it may be incorporated in the spring element, and both stress breaking layer 47 and said position adjusting mechanism are fabricated between said connecting portion 46 and said dental corona 48 in another instance.

Figure 15:
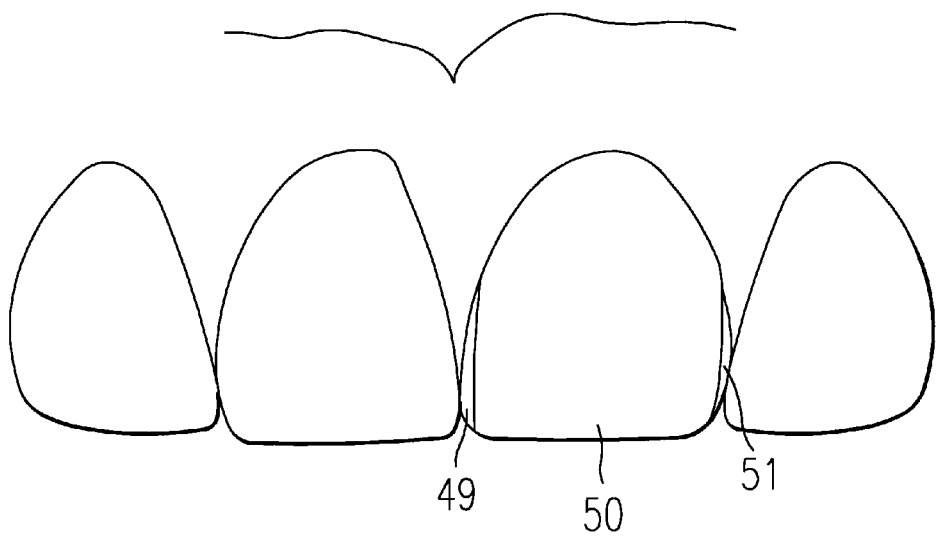
FIG. 15 shows a front view of four anterior teeth at the labial side in an embodiment of the artificial teeth of this invention.

As for the embodiment of this invention illustrated in FIG. 15, provided are the stress breaking layer at a mesial proximal surface 49 and the stress breaking layer at a distal proximal surface 50. The same pressure buffering materials as the dental corona are used at said distal and mesial surfaces of the artificial anterior tooth of this invention.

Said structure of this invention enables the artificial anterior tooth to move freely so as to get a stable occlusion, not being affected by the neighboring teeth when said dental corona is to move as a result of the occlusal pressure.

Figure 16:
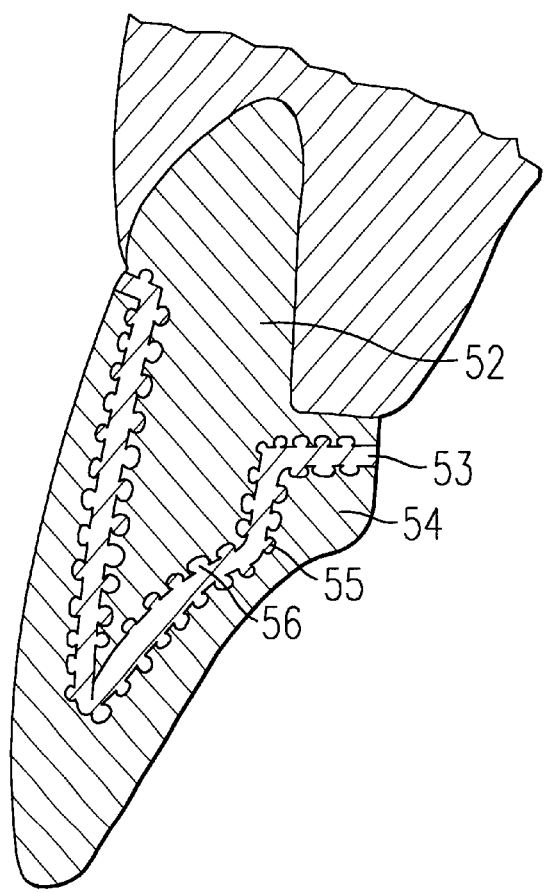
FIG. 16 shows a vertical sectional view of an anterior tooth in an embodiment of the artificial teeth of this invention.

As for the embodiment of this invention illustrated in FIG. 16, the artificial anterior tooth is reinforced as a result of holding holes, because a stress breaking layer 53 of the artificial anterior tooth, made up of pressure buffering materials capable of elongating and shrinking smoothly, is connected mechanically with much stronger force with a connecting portion 52 and the dental corona of a lingual portion 54.

Figure 17:
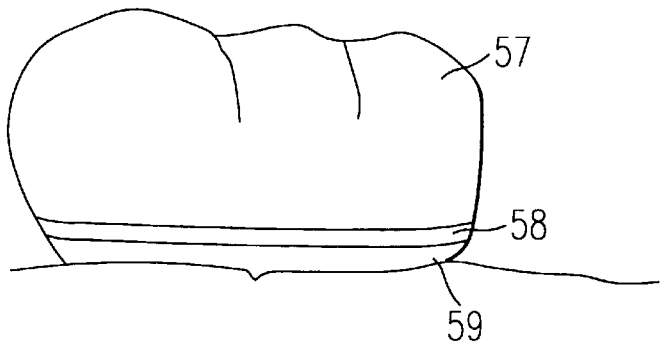
FIG. 17 shows a front view of a molar tooth at a buccal side in an embodiment of the artificial teeth of this invention.

In the embodiment of this invention illustrated in FIG. 17, this figure is a front view of FIG. 1 as shown beforehand, showing the artificial molar tooth, i.e. it is the artificial molar tooth consists of an occlusal surface portion 57, a stress breaking layer 58, and a connecting portion 59.

Said stress breaking layer 58 deforms itself elastically and said occlusal surface portion 57 moves and sinks to a small extent when said occlusal surface portion receives the occlusal pressure.

Figure 18:
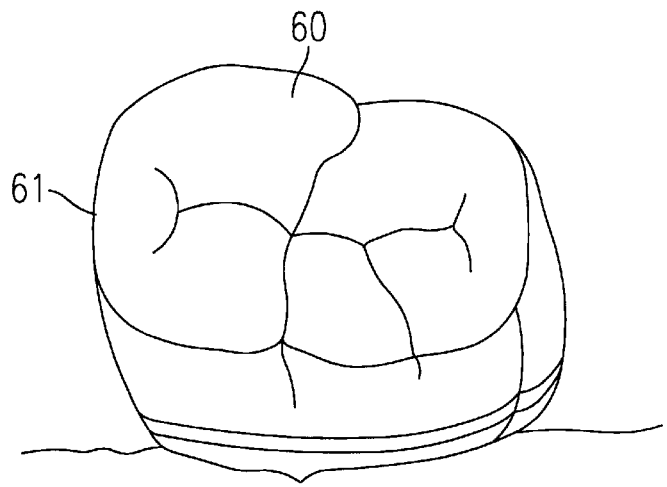
FIG. 18 shows a three-dimensional view of a molar tooth at a buccal side in an embodiment of the artificial teeth of this invention.
Figure 19:
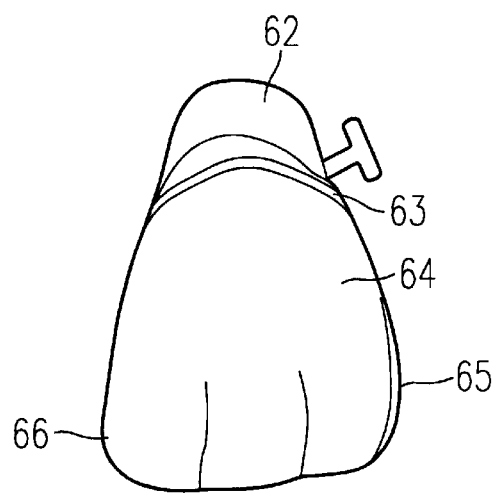
FIG. 19 shows a front view of anterior tooth at the labial side in an embodiment of the artificial teeth of this invention.
Figure 20:
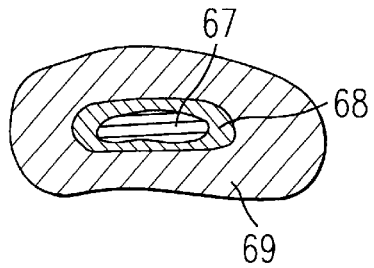
FIG. 20 shows the cross-sectional view, E—E, of an anterior tooth as shown in FIG. 11 illustrated beforehand in an embodiment of the artificial teeth of this invention.

FIG. 18 is a three dimensional view of FIG. 1.
FIG. 19 is a three dimensional view of FIG. 11.
FIG. 20 is a cross sectional view of FIG. 11.

A stress breaking layer 68 made up of pressure buffering materials, capable of elongating and shrinking smoothly, deforms itself elastically absorbing the occlusal pressure that a dental corona 69 receives because it is incorporated between said dental corona 69 and a connecting portion 67 so as to make them en bloc.

Thus, when an early contact occurs, the dental corona moves and sinks downwards to a small extent, the whole remaining teeth and/or artificial teeth set out the occlusal equilibration.

Figure 21:
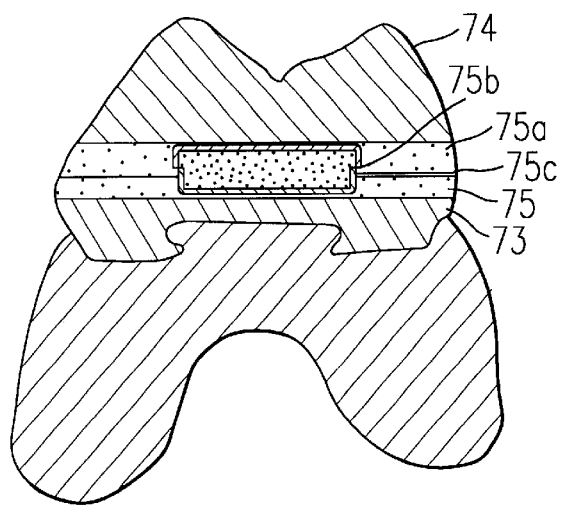
FIG. 21 shows a vertical sectional view of a molar tooth in an embodiment of the artificial teeth of this invention.

FIG. 21 shows a cross sectional view thereby how the artificial molar tooth is formed, however, a stress breaking layer 75 is shown as emphasized so as to give better explanation.

Said stress breaking layer 75 made up of pressure buffering materials capable of elongating and shrinking smoothly is provided between an occlusal surface portion 74 and a connecting portion 73.

Said stress breaking layer 75 consisting of a synthetic plastic product 75a as the mass element and also at least one shock absorber 75b is fabricated as the spring element, and also an attached bar 75c being an extension bar extended from said spring element that is connected with the outside portion of the dental corona.

The artificial molar tooth in which the intensity of the stress of the shock absorbers of the artificial molar tooth in this invention is to meet the occlusal pressure, being adjustable by means of turning said extension bar 75c either in the right direction or left direction.

As for the mass element of said stress breaking layer 75, also used are composite materials, rubber and its analogs other than said synthetic plastic product 75a.

As for the function of said shock absorber 75b, it is capable of adjusting the intensity of the stress that is required to meet the occlusal pressure.

In addition to said adjusting function of the intensity of the stress to meet the occlusal pressure, it has another adjusting function of the occlusal surface portion enabling said occlusal surface portion 74 to move freely, including vertical, horizontal, and oblique movements thereof.

The number of shock absorber is either single or plural. For example, four shock absorbers are used at a lower portion of the cusp of four cusps, two of the lingual cusp side at a lower portion in the case of the maxillary molar tooth, thus the occlusal plane of the occlusal surface will be well adjusted.

Figure 22:
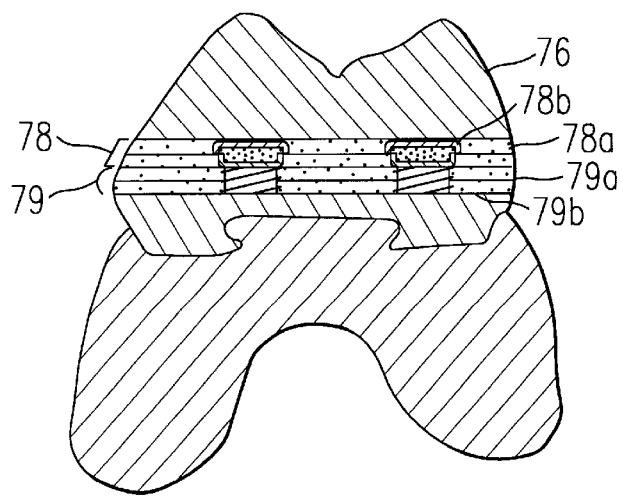
FIG. 22 shows a vertical sectional view of a molar tooth in an embodiment of the artificial teeth of this invention.

FIG. 22 shows the cross sectional view of an artificial molar tooth. Artificial molar tooth that is provided with a stress breaking layer 78 made up of pressure buffering materials capable of elongating and shrinking smoothly, and an adjusting mechanism 79 between an occlusal surface portion 76 and a connecting portion 77.

As for said stress breaking layer 78, it consists of either the mass element or the spring element in a case, and otherwise consists of combinations of the mass element and spring element and of both mass element and spring element with additional spring element.

Furthermore, it may have an extension bar 78a extended from a shock absorber 78b, allowing to adjust the intensity of the stress to meet the occlusal pressure by means of turning said extension bar 78a either in the right direction or the left direction.

In this invention contained is a movement-adjusting gear 79b in an artificial tooth being incorporated in an adjusting mechanism 79 capable of adjusting movement of said occlusal surface portion 76 including vertical, horizontal, and/or oblique movement and said adjusting gear 79b is adjustable by turning said extension bar 79b with an operation from the outside of the denture corolla.

When the shock absorber 78b in said stress breaking layer 78 and said movement adjusting gear 79b in the adjusting mechanism are not located at the place right below said occlusal surface portion, a hard pedestal is provided between said stress breaking layer 78 and said adjusting mechanism 79.

As for the shock absorber and the movement adjusting gear, the number of them is used both in single and plural.

Figure 23:
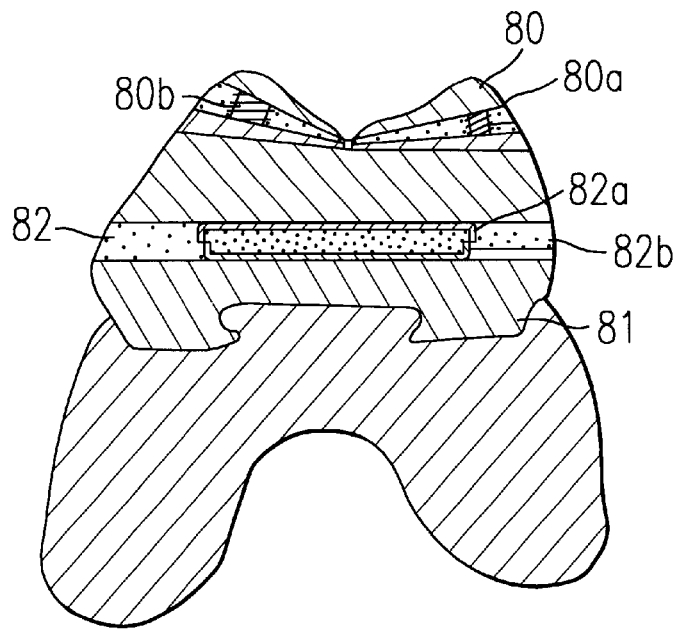
FIG. 23 shows a vertical sectional view of a molar tooth in an embodiment of the artificial teeth of this invention.

FIG. 23 is showing the cross sectional view of an artificial molar tooth characterized in principle in that a stress breaking layer 82, made up of pressure buffering materials capable of elongating and shrinking smoothly, is provided between an occlusal surface portion 80 and a connecting portion 81, where the cusp angle of said occlusal portion 80 is adjustable.

Said occlusal surface portion 80, whose cusp angle being adjustable, consists of an extension bar 80b extended from a cusp angle adjusting gear 80a that is provided in said occlusal surface portion 80 to the surface of the dental corona, and turning said extension bar 80b either right or left enables the cusp angle to be adjusted smoothly.

As for the adjustment of the cusp angle, the cusp angles at the buccal side and the lingual side are adjustable with the same degree, otherwise with different angles at the buccal sides and lingual side, or further with the mechanism capable of adjusting the angle of each side separately and independently.

As for said stress breaking layer 82, one case in which it is composed of the mass element such as rubber and its analogs, and synthetic plastics, and another case in which at least one of the spring element such as the shock absorbers and the springs are used.

Another case in which combinations of the mass element and spring element, i.e. combinations of, for example, synthetic plastics products and shock absorbers.

Still another case in which provided is, for example, a shock absorber 82a as the spring element capable of adjusting the intensity of the stress to meet the occlusal pressure at said stress breaking layer 82, and also an extension bar 82b extended straightly from said shock absorber 82a to the surface of the dental corona is provided, and this is another mechanism of this invention that the adjustment of the intensity of the stress can be performed by turning said extension bar 82b either right or left.

Furthermore, another mechanism capable of moving freely including vertical, horizontal, and/or oblique movement, is provided in the shock absorbers so that adjustment of the position movement of the occlusal surface portion is smoothly performed.

The number of shock absorber used in this invention is either singular or plural.

Figure 24:
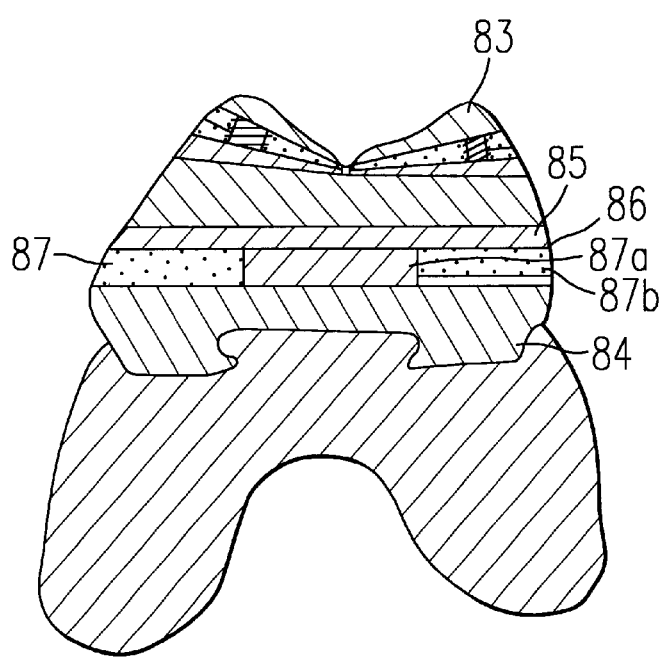
FIG. 24 shows a vertical sectional view of a molar tooth in an embodiment of the artificial teeth of this invention.

FIG. 24 shows the cross sectional view of an artificial molar tooth.

A stress breaking layer 85, made up of pressure buffering materials capable of elongating and shrinking smoothly, a hard pedestal 86 and at least one of the movement-adjusting gear 87a that enables an occlusal surface portion 83 to move freely, including vertical, horizontal, and/or oblique movement, are incorporated between said occlusal surface portion 83, whose cusp angle being adjustable, and a connecting portion 84. And plurality of movement-adjusting extension bar 87b are provided in the manner of function-wise in a case, and only one of them is provided multi-functionally in another case.

The artificial molar tooth with an adjusting mechanism 87 that is characterized in that each adjustment is achieved by turning the extension bar either right or left.

Said stress breaking layer 85 is formed with the mass element such as composite materials, rubber and its analogs, and synthetic plastics in a case, and is formed with combinations of the mass element and the spring element such as shock absorbers with an additional mechanism capable of meeting the variety of intensity of the occlusal pressure in another case.

Furthermore, in addition to said mechanism capable of meeting the variety of intensity of the occlusal pressure, another shock absorber capable of adjusting the movement and enabling the occlusal surface portion to move freely including vertical, horizontal, and/or oblique movement, is provided in said shock absorbers in another case.

The shock absorbers are employed in either singular or plural number.

Figure 25:
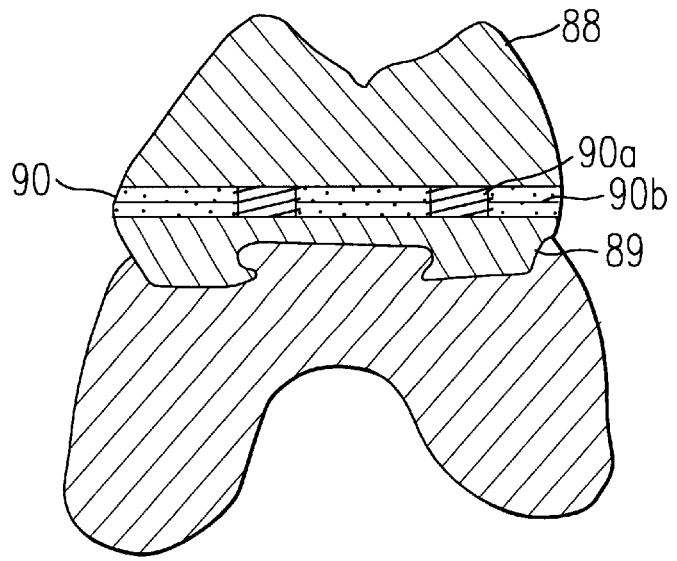
FIG. 25 shows a vertical sectional view of a molar tooth in an embodiment of the artificial teeth of this invention.

FIG. 25 shows the cross sectional view of an artificial molar tooth concerning claim 25 of this invention. At least one of movement adjusting gear 90a being capable of enabling an occlusal surface portion 88 to move at least one of the movements, i.e. vertical, horizontal, and/or oblique movement, is provided between said occlusal surface portion 88 and a connecting portion 89, and turning an extension bar 90b either right or left enables said occlusal surface portion 88 to adjust movements, for example, vertical movement. Said extension bar 90b is extending straight from said movement adjusting gear 90a to the surface of the dental corona.

Said extension bar 90b is employed in plurality to meet each activity independently in a case, and only one extension bar 90b is to meet the various kinds of adjustments in another case.

Figure 26:
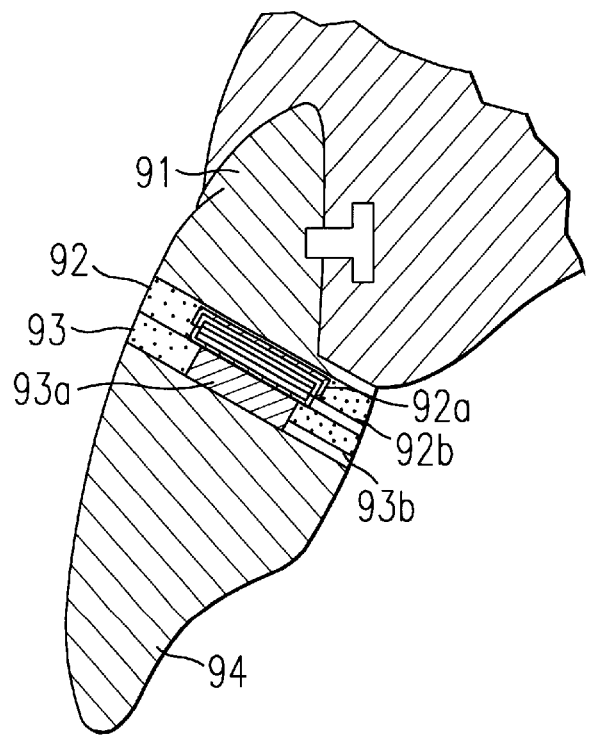
FIG. 26 shows a vertical sectional view of an anterior tooth in an embodiment of the artificial teeth of this invention.

The embodiment of this invention illustrated in FIG. 26 shows the cross sectional view of an artificial anterior tooth.

Said embodiment of the invention is in principle concerning the artificial anterior tooth in which provided are a stress breaking layer 92 made up of the pressure buffering materials capable of elongating and shrinking smoothly and an adjusting mechanism 93 capable of adjusting the smooth movement of the dental corolla.

Said stress breaking layer 92 employs the mass element such as composite materials, rubber and its analogs, and synthetic plastics in an instance, and the spring element such as springs, and combinations of the mass element and spring element in another instance, respectively.

In addition to it, at least one shock absorber 92a, capable of adjusting the variety of intensity of the stress to meet the variable occlusal pressure, is provided in said spring element, and an adjusting extension bar 92b extending from said shock absorber to the surface of the dental corona, and turning said adjusting extension bar 92b either right or left enables the occlusal surface portion to adjust so as to meet the given occlusal pressure.

At least one of the movement adjusting gear 93a being capable of enabling the dental corona to move smoothly, including vertical, horizontal, and/or oblique movement, is provided in an adjusting mechanism 93, and at least one extension bar 93b extending continuously from said movement adjusting gear 93a to the surface of the dental corona is provided, and turning said extension bar(s) 93b either in the right direction or left direction enables the dental corona to move smoothly.

Otherwise, another movement adjusting mechanism being capable of adjusting vertical movement, horizontal movement, and/or oblique movement of the dental corona is provided in said shock absorber 92a.

Figure 27:
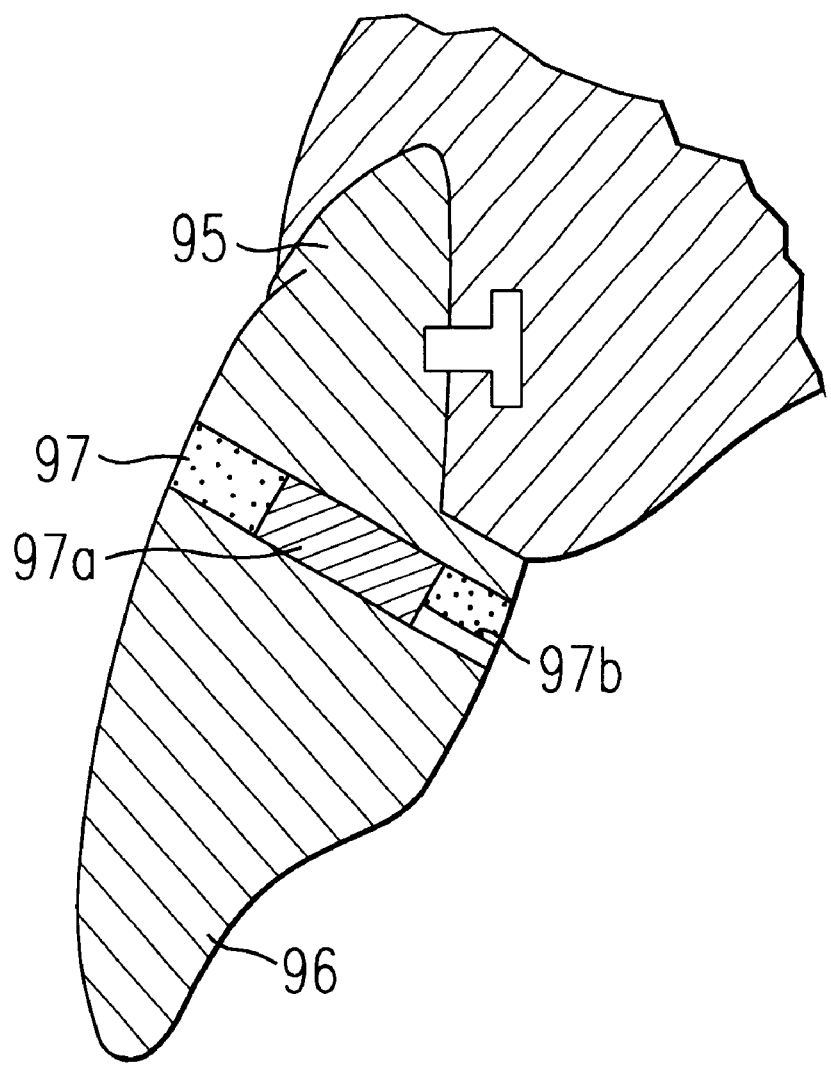
FIG. 27 shows a vertical sectional view of an anterior tooth in an embodiment of the artificial teeth of this invention.

The embodiment of this invention illustrated in FIG. 27 is showing an artificial anterior tooth, in which an adjusting mechanism 97 being capable of enabling a dental corolla 96 to adjust the vertical movement, horizontal movement, and/or oblique movement is provided between a connecting portion 95 attached solidly to the alveolar portion of the denture base, and said dental corona 96.

At least one of the movement adjusting gear 97a being capable of movement adjusting is provided in said adjusting mechanism 97, and an extension bar 97b extending continuously from said adjusting mechanism 97 to the surface of the dental corona is also provided, and it is possible that turning said extension bar 97b either right or left enables said dental corona to perform any of the adjustments.

The movement adjusting gears are employed in plurality for each of adjustments in a case, and only one of said movement adjusting gears is employed to perform all various adjustments by itself in another case.

As described beforehand in this specification, the artificial teeth prepared in this invention are favorable for every person and offer a great deal of benefits to human beings as they are capable of providing much better occlusal equilibration in the prosthetic restoration of all kinds of the dental defects.

What is claimed is:

1. A dental prosthesis for artificial molar tooth, comprising a stress breaking layer, made of pressure buffering materials capable of elongating and shrinking smoothly and an adjustment mechanism configured to adjust the strength of a spring thereof, and provided between an occlusal surface portion receiving directly the biting pressure, and a connecting portion fixed firmly to the alveolar portion of a denture base.

2. The dental prosthesis for artificial molar tooth defined in claim 1, wherein the occlusal surface is divided into an inner dental corona and an outer dental corona, said divided pieces of the dental corona are combined with pressure buffering materials capable of elongating and shrinking smoothly, being unified with the stress breaking layer.

3. The dental prosthesis for artificial molar tooth defined in claim 1, wherein at least one of side of the stress breaking layer, of a mesial proximal surface layer or a distal proximal layer, is composed of pressure buffering materials capable of elongating and shrinking smoothly.

4. The dental prosthesis for artificial molar tooth defined in claim 1, wherein the occlusal surface portion has concave part(s) provided inside the occlusal surface portion capable of sinking downwards or upwards by the biting pressure, and the connection portion also has convex part(s) against the occlusal surface portion.

5. The dental prosthesis for artificial molar tooth defined in claim 1, wherein the occlusal surface portion can have holding holes facing a stress breaking layer, and the connecting portion can also have holding holes facing said stress breaking layer, said holding holes are bound strongly with said stress breaking layer capable of elongating and shrinking smoothly.

6. A dental prosthesis for artificial molar tooth, comprising an occlusal surface portion receiving directly the biting pressure, and a stress breaking layer, made of pressure buffering materials capable of elongating and shrinking smoothly and an adjustment mechanism configured to adjust the strength of a spring thereof, and whose part being fixed firmly to the alveolar portion of a denture base.

7. A dental prosthesis for artificial anterior tooth, comprising a stress breaking layer made of pressure buffering materials capable of elongating and shrinking smoothly and an adjustment mechanism configured to adjust the strength of a spring thereof, which is provided between a connecting portion planted firmly in the alveolar portion of a denture base, and a distal corona of the artificial anterior tooth.

8. The dental prosthesis for artificial anterior tooth of claim 7, wherein the tooth has at least a stress breaking layer at one side of mesial proximal surface of the tooth and/or a stress breaking layer at one side of distal proximal surface of said tooth.

9. The dental prosthesis for artificial anterior tooth of claim 7, wherein the connection portion fixed firmly to the denture base has holding holes facing the stress breaking layer connecting the portion firmly with the stress breaking layer, and connecting the dental corona firmly with the stress breaking layer.

10. The dental prosthesis for artificial anterior tooth, comprising a stress breaking layer made of pressure buffering materials capable of elongating and shrinking smoothly and an adjustment mechanism configured to adjust the strength of a spring thereof, which is provided between a connecting portion connected firmly to a denture base and a dental corona of the anterior tooth.

11. The dental prosthesis for artificial molar tooth, comprising a stress breaking layer capable of adjusting the strength of a spring thereof, made of non-metallic spring element, which is provided between a connecting portion connected firmly to the alveolar portion of a denture base and an occlusal surface portion receiving directly the biting pressure.

12. The dental prosthesis for artificial molar tooth according to claim 11, wherein the tooth has at least the stress breaking layer at one side of mesial proximal surface and/or distal proximal surface of said tooth, where said stress breaking layer(s) are composed of pressure buffering materials capable of elongating and shrinking smoothly.

13. The dental prosthesis for artificial molar tooth, comprising a mechanism capable of adjusting the dental corona (s) to move vertically and horizontally by an operation from the outside of said dental corona(s), and a stress breaking layer, which is provided between the occlusal surface portion and the connecting portion.

14. The dental prosthesis for artificial molar tooth according to claim 13, wherein the tooth has one of stress breaking layers, made of pressure buffering materials capable of elongating and shrinking smoothly, at least at one side of a tooth, where said stress breaking layer or layers are provided at either mesial proximal surface or distal proximal surface, or at both surfaces.

15. The dental prosthesis for artificial molar tooth, comprising an adjusting mechanism capable of adjusting vertical movement and horizontal movement of an occlusal portion, which is provided between the occlusal surface portion receiving directly the biting pressure, and a connecting portion connected firmly to the alveolar portion of a denture base.

16. The dental prosthesis for artificial molar tooth according to claim 15, wherein the tooth has at least one of said stress breaking layers, at either mesial proximal surface or distal proximal surface, or at both surfaces of said molar tooth, where said stress breaking layers are composed of pressure buffering materials capable of elongating and shrinking smoothly.

17. The dental prosthesis for artificial anterior tooth, comprising a stress breaking layer, made of pressure buffering materials capable of elongating and shrinking smoothly, an adjusting mechanism capable of adjusting the vertical movement and horizontal movement by an operation from the outside which are provided between a connecting portion and a dental corona.

18. The dental prosthesis for artificial anterior tooth according to claim 17, wherein the tooth has at least one of said stress breaking layers, at either mesial proximal surface or distal proximal surface, or at both surfaces of said anterior tooth, where said stress breaking layers are composed of pressure buffering materials capable of elongating and shrinking smoothly.

19. The dental prosthesis for artificial anterior tooth, comprising an adjusting mechanism capable of adjusting the free vertical movement and the free horizontal movement of said occlusal surface portion, which is set up between a connecting portion and a dental corona.

20. The dental prosthesis for artificial anterior tooth according to claim 19, wherein the tooth has at least one of said stress breaking layers, at either mesial proximal surface or distal proximal surface, or at both surfaces of said anterior tooth, where said stress breaking layers are composed of pressure buffering materials capable of elongating and shrinking smoothly.

21. The dental prosthesis for artificial molar tooth, comprising an adjusting mechanism capable of adjusting the position of said occlusal portion, which has at least one of the functions capable of adjusting at least one of movements including vertical, horizontal, and/or oblique movement of the occlusal surface portion, which is provided between the occlusal surface portion receiving the occlusal pressure, and the connecting portion connected firmly to the alveolar portion of a denture base.

22. The dental prosthesis for artificial molar tooth, comprising an adjusting mechanism capable of adjusting freely the vertical, horizontal, and/or oblique movement of the occlusal surface portion, and a stress breaking layer, made of pressure buffering materials capable of elongating and shrinking smoothly, which are set up between the connecting portion receiving directly said occlusal pressure, and the connecting portion, where said occlusal surface potion is capable of moving or sinking downwards by deforming itself elastically, and moreover said adjusting mechanism can be adjusted while the client rests, thus allowing the position of said occlusal surface portion to be properly adjusted.

23. The dental prosthesis for artificial molar tooth according to claim 22, wherein the tooth has a stress breaking layer, made of pressure buffering materials, capable of adjusting its stress to meet the variable intensity of said occlusal pressure.

24. The dental prosthesis for artificial anterior tooth, comprising a stress breaking layer, made of pressure buffering materials capable of elongating and shrinking smoothly and an adjustment mechanism configured to adjust the strength of a spring thereof, which is set up between the connecting portion, connected firmly to the alveolar portion of a denture base, and the dental corona, where said dental corona is capable of moving and sinking downwards when it receives said occlusal pressure as said stress breaking layer deforms itself elastically.

25. The dental prosthesis for artificial anterior tooth according to claim 24, wherein the tooth has a stress breaking layer, made of pressure buffering materials capable of elongating and shrinking smoothly, is capable of deforming itself elastically to meet variable intensity of the occlusal pressure, and moreover the intensity of the compression strength of said stress breaking layer is adjustable by an operation from the outside.

26. The dental prosthesis for artificial anterior tooth, comprising an adjusting mechanism allowing the position of the dental corona to move vertically, horizontally, and/or obliquely, and at the same time being adjustable by an operation from the outside while the client rests, which is provided between the connecting portion, connected firmly to the alveolar portion of a denture base, and the dental corona.

27. The dental prosthesis for artificial anterior tooth, comprising a stress breaking layer, made of pressure buffering materials capable of elongating and shrinking smoothly, and an adjustment mechanism capable of free-moving including vertical, horizontal, and/or oblique movement, and furthermore adjusting the position of the dental corona smoothly while the client rests which are provided between the connecting portion connected firmly to the alveolar portion of a denture base, and the dental corona, where said stress breaking layer, made of pressure buffering materials capable of elongating and shrinking smoothly, deforms itself elastically, thus said dental corona is able to sink downwards when it receives said occlusal pressure of said artificial molar tooth.

28. The dental prosthesis for artificial anterior tooth according to claim 27, wherein the tooth has a stress breaking layer, made of pressure buffering materials capable of elongating and shrinking smoothly, whose stress to meet variable occlusal pressure can be adjustable by an operation from the outside.

29. The dental prosthesis for artificial molar tooth, comprising a stress breaking layer, made of pressure buffering materials capable of elongating and shrinking smoothly, which is provided between the occlusal surface portion and the connecting portion in parallel to the occlusal surface portion, where the stress breaking layer, made of pressure buffering materials capable of elongating and shrinking smoothly, comprises; (i) pressure buffering materials as the mass element, (ii) combinations of said mass element and a spring element, (iii) further including an adjusting mechanism to adjust buffering force against said spring element, (iv) in addition further, having at least one function out of various adjusting movements such as rising up, falling down, horizontal movement and oblique movement, (v) in addition again, having overall functions of adjustment of vertical, horizontal, and oblique movements of said occlusal surface portion.

30. The dental prosthesis for artificial anterior tooth, comprising a stress breaking layer, made of pressure buffering materials capable of elongating and shrinking smoothly, which is provided between the occlusal surface portion and the connecting portion in parallel to the occlusal surface portion, where the stress breaking layer, composed of pressure buffering materials capable of elongating and shrinking smoothly, comprises; (i) pressure buffering materials as the mass element, (ii) combinations of said mass element and said spring element, (iii) further including an adjusting mechanism to adjust buffering force against said spring element, (iv) in addition further, having at least one function out of various adjusting movements such as rising up, falling down, horizontal movement and oblique movement, (v) in addition again, having overall functions of adjustment of vertical, horizontal, and oblique movements of said occlusal surface portion.

* * * * *